US00PP09030P

United States Patent [19]

Dudeck

[11] Patent Number: Plant 9,030

[45] Date of Patent: Jan. 3, 1995

[54] BERMUDAGRASS PLANT 'FHB-135'

[75] Inventor: Albert E. Dudeck, Gainesville, Fla.

[73] Assignee: Florida Foundation Seed Producers, Inc., Greenwood, Fla.

[21] Appl. No.: 982,954

[22] Filed: Nov. 30, 1992

[51] Int. Cl.[6] ..... A01H 5/00
[52] U.S. Cl. ..... Plt./90
[58] Field of Search ..... Plt. 90

*Primary Examiner*—James R. Feyrer
*Attorney, Agent, or Firm*—William M. Hobby, III

[57] ABSTRACT

A dwarf, rapid spreading, stoloniferous bermudagrass which has use on golf course putting greens, lawn bowls, grass tennis courts, and other turf areas where an extremely fine textured, low growing turf is desired. The grass has an improved density and winter color over the commercially available Tifdwarf cultivar of bermudagrass. The grass is clearly differentiated from Tifdwarf bermudagrass by DNA fingerprints generated through the use of multiplex DNA amplification fragment length polymorphism techniques.

3 Drawing Sheets

BACKGROUND OF THE INVENTION

The present invention relates to a new and distinct cultivar of bermudagrass, tested as FHB-135, which was discovered by the Inventor in the State of Hawaii. It is one of 225 clonal selections of off-type bermuda grasses collected throughout the state of Hawaii in 1988. The golf course putting green on which it was found was originally planted in Tifgreen bermudagrass in 1977. Bermudagrass FHB-135 is a dwarf, rapid spreading, stoloniferous turfgrass for use on golf course putting greens, lawn bowls, grass tennis courts, and other turf areas where an extremely fine textured, low growing turf is desired.

DRAWINGS

Figure 1:
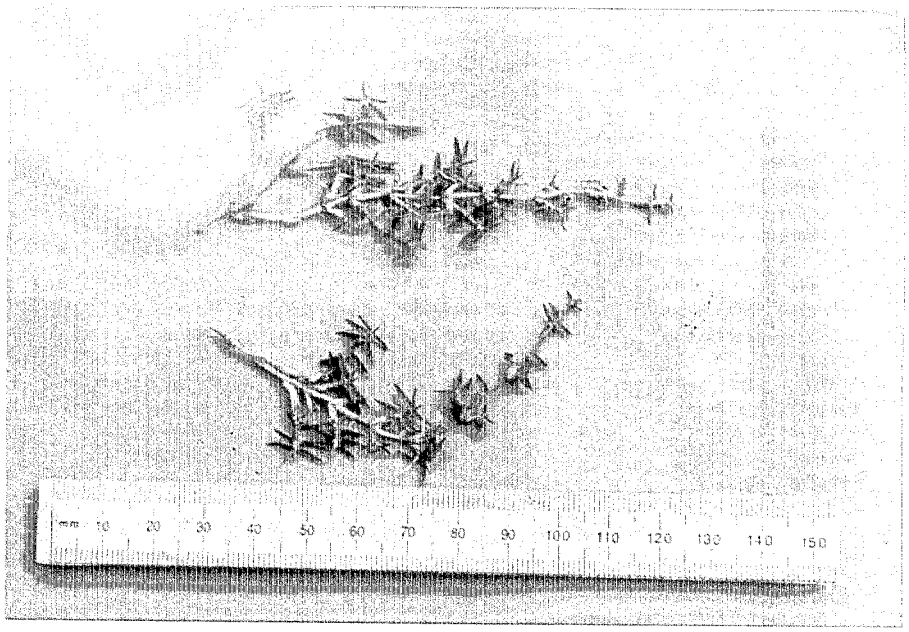
FIG. 1 is a color photograph of a typical specimen of my new bermudagrass.
Figure 2:
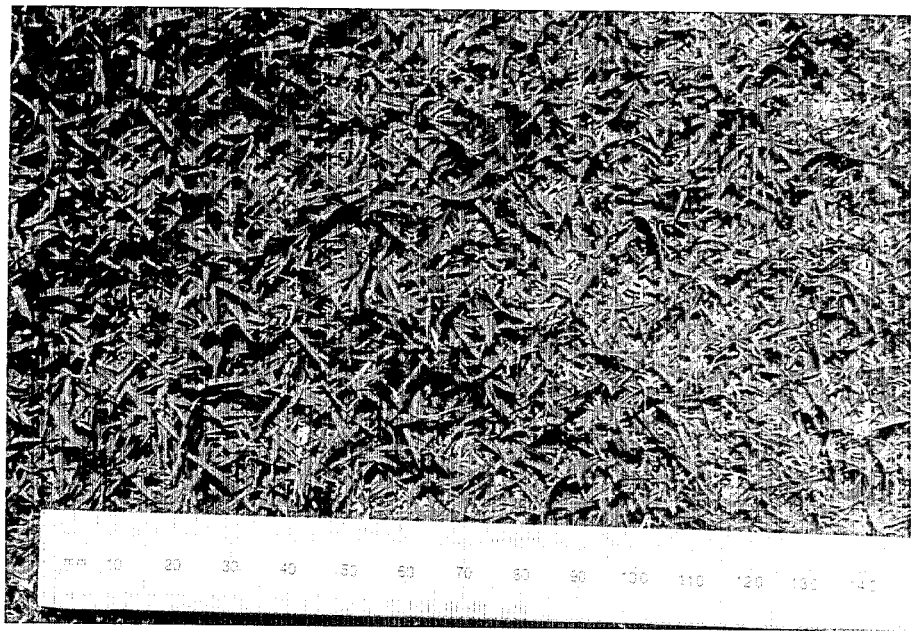
FIG. 2 is another color photograph of a typical specimen of my new bermudagrass.
Figure 3:
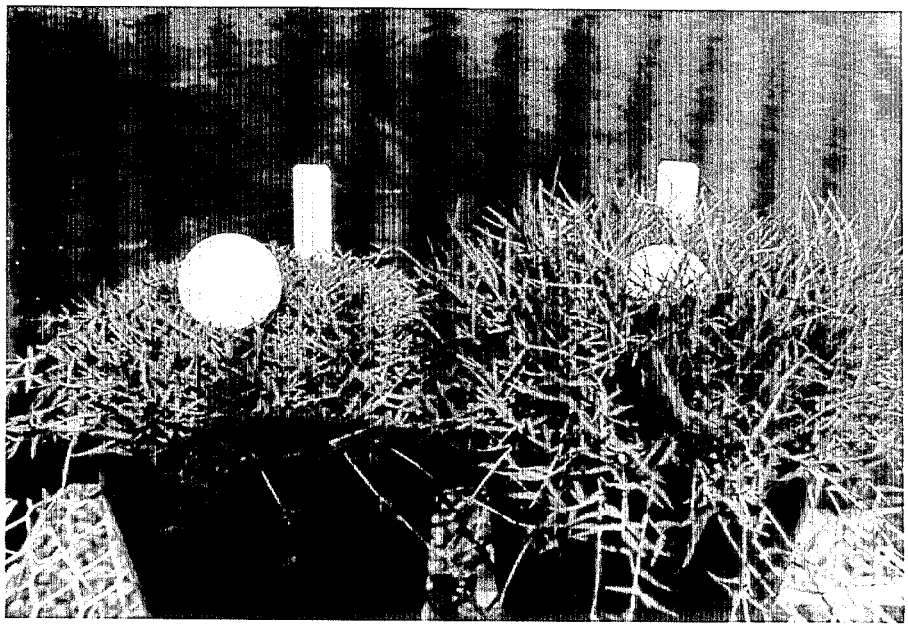
Figure 4:
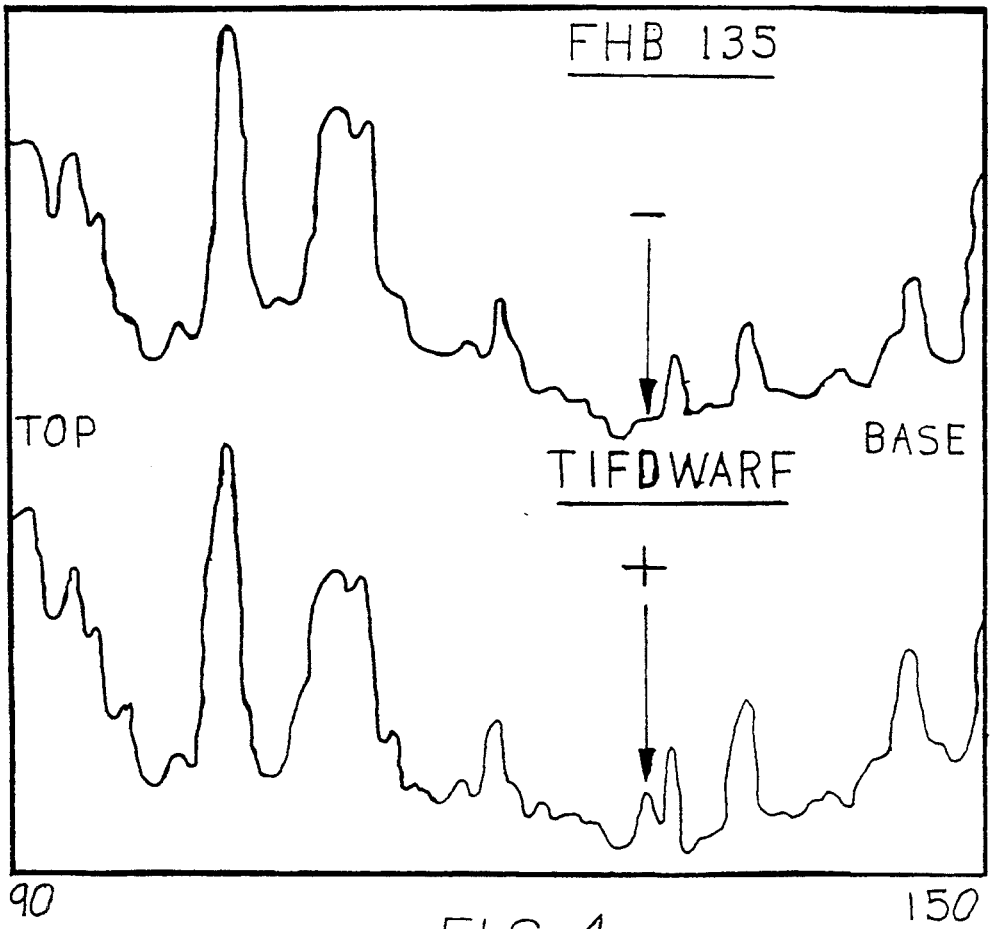

FIG. 3 is a color photograph which contrasts the fine textured foliage and short stolons of FHB-135 (on left) with Tifdwarf bermudagrass (on right); and FIG. 4 is a desitometric scan of the deoxyribonucleic acid (DNA) amplification profiles of bermudagrass FHB-135 and Tifdwarf bermudagrass and shows that bermudagrass FHB is differentiated from Tifdwarf bermudagrass by DNA fingerprints generated through the use of multiplex DNA amplification fragment length polymorphism techniques.

DETAILED DESCRIPTION OF THE PLANT

Bermudagrass FHB-135 is a selected mutant form presumably from the Tifgreen cultivar of *Cynodon dactylon* (L.) Pers. × *C. transvallensis* Burtt-Davy. It is an inconspicuous flowering, sterile dwarf, fine textured, creeping grass which spreads only by means of stolons. It produces no rhizomes. Its growth habit resembles that of Tifdwarf bermudagrass. Its fine leaf texture and dwarf habit of growth are due to its very short, narrow leaf blades produced on short stolons with many, very short internodes. It retains its green color during the winter unlike Tifdwarf bermudagrass which takes on an undesirable, purple appearance. Size of its leaf blade is responsive to photoperiod. It produces shorter, narrower leaf blades in winter compared to longer, wider leaf blades in summer.

Bermudagrass FHB-135 has been propagated vegetatively by sprigs into a plot 15 by 24 meters in size during the summer of 1991 in Alachua County, Fla. adjacent to a plot of Tifdwarf bermudagrass for comparison with the following observations.

(a) Bermudagrass FHB-135 had improved density and winter color over the commercially available Tifdwarf cultivar of bermudagrass.

(b) Bermudagrass FHB-135 retained its moderate olive green color, Munsell color designation, 5GY 4/3, during the winter which is unlike Tifdwarf bermudagrass which takes on an undesirable, deep purple color, Munsel color designation, 7.5P3/9. Munsell color designation was obtained using a Nickerson color fan. Color is subject to variation depending on the environmental conditions under which the grass is grown.

(c) When maintained at a mowing height of 6 mm, under low fertility (no fertilization for six weeks prior to examination), and under a long-day photoperiod (14 h), the average length of a fully matured leaf blade of bermudagrass FHB-135 was 6.5 mm while Tifdwarf bermudagrass averaged 8.2 mm in length. Leaf width averaged 1.4 mm and was not different between grasses.

(d) Under long days of 13 hours, bermudagrass FHB-135 had a shorter leaf blade of 14.2 mm in length compared to 17.4 mm for Tifdwarf bermudagrass. Leaf blade width was not different between grasses and averaged 2.2 mm. Furthermore, under short days of 9 hours, bermudagrass FHB-135 had shorter and narrower leaf blades of 11.2 mm in length and 2.08 mm in width. Tifdwarf bermudagrass on the other hand had leaf blades which averaged 17.0 mm in length and 2.26 mm in width under the same conditions. Leaf blades on Tifdwarf bermudagrass were not affected by photoperiod. It averaged 17.2 mm in length and 2.22 mm in width when averaged over long and short photoperiods. Bermudagrass FHB-135, however, was markedly influenced by photoperiod. It had shorter and narrower leaf blades under short days compared to long days.

(e) Rate of growth and ground cover from plugs planted on 30 cm centers in a field on 21 May, 1991 were monitored over a 90-day period. Plots were unmowed, but a complete N-P-K fertilizer was applied biweekly at the rate of 2.5 g N $m^{-2}$. After 90 days, the unmowed height of Tifdwarf bermudagrass averaged 1.7 cm while bermudagrass FHB-135 averaged 0.8 cm. Grasses were not significantly different, however, from each other in unmowed shoot height.

(f) Mean stolon number and length per 10 cm plug at 30 days after planting wer not different between bermudagrass FHB-135 and Tifdwarf Bermudagrass. They averaged 21.6 total stolons per plug with an average stolon length of 1.06 cm.

(g) Ground cover estimates, rate of ground cover, and days to 50% ground cover during the 90-day study showed no differences between bermudagrass FHB-135 and Tifdwarf bermudagrass indicating that their establishment rates are comparable.

(h) Bermudagrass FHB-135 had shorter internodes than either Tifdwarf or Tifgreen bermudagrass. Average internode length for the three cultivars was 8, 12, and 25 mm, respectively.

(i) When grown at different N levels of fertilization, both grasses responded similarly. However, Tifdwarf had a shoot growth rate which was 2.4 times greater than that of bermudagrass FHB-135. Turf quality in both grasses was differentially affected by N fertilization. At levels greater that 1.5 g N $m^{-2}$, bermudagrass FHB-135 had superior turf quality.

(j) Seed head production during July and August of 1992 was not different between bermudagrass FHB-135 and Tifdwarf bermudagrass. They averaged $17.7 \pm 28.1$ inflorescences $m^{-2}$ with $2.84 \pm 0.63$ branches per inflorescence. Neither grass produced viable seed.

(k) Bermudagrass FHB-135 became thatchy over time, but since its establishment rate was equal to that of Tifdwarf bermudagrass in terms of stolon number and length as well as in ground cover production, its increased density was due to its shorter internodes.

(l) Bermudagrass FHB-135 has been asexually reproduced by me by plugging, sprigging, and sodding.

I claim:

1. A new and distinct cultivar of bermudagrass plant, substantially as herein illustrated and described, characterized particular by the fine texture of the leaf blade and which produces a low growing turf of improved density and winter color.

* * * * *